US010392657B2

(12) United States Patent
Klein et al.

(10) Patent No.: US 10,392,657 B2
(45) Date of Patent: Aug. 27, 2019

(54) METHOD AND KIT FOR DETERMINING THE GENOME INTEGRITY AND/OR THE QUALITY OF A LIBRARY OF DNA SEQUENCES OBTAINED BY DETERMINISTIC RESTRICTION SITE WHOLE GENOME AMPLIFICATION

(71) Applicants: Menarini Silicon Biosystems S.p.A., Castel Maggiore (IT); Fraunhofer-Gesellschaft Zur Foerderung Der Angewandten Forschung E.V., München (DE)

(72) Inventors: Christoph Andreas Klein, Regensburg (DE); Bernhard Michael Polzer, Munich (DE); Nicolò Manaresi, Bologna (IT)

(73) Assignees: Menarini Silicon Biosystems S.p.A., Castel Maggiore (IT); Fraunhofer-Gesellschaft Zur Förderung Der Angewandten Forschung E.V., München (DE)

( * ) Notice: Subject to any disclaimer, the term of this patent is extended or adjusted under 35 U.S.C. 154(b) by 343 days.

(21) Appl. No.: 15/101,299

(22) PCT Filed: Dec. 4, 2014

(86) PCT No.: PCT/IB2014/066602
§ 371 (c)(1),
(2) Date: Jun. 2, 2016

(87) PCT Pub. No.: WO2015/083121
PCT Pub. Date: Jun. 11, 2015

(65) Prior Publication Data
US 2018/0187254 A1 Jul. 5, 2018

(30) Foreign Application Priority Data
Dec. 4, 2013 (EP) .................................. 13195770

(51) Int. Cl.
*C12Q 1/68* (2018.01)
*C12P 19/34* (2006.01)
*C12Q 1/6869* (2018.01)
*C12Q 1/686* (2018.01)
*C40B 30/00* (2006.01)
*C40B 40/06* (2006.01)

(52) U.S. Cl.
CPC .......... *C12Q 1/6869* (2013.01); *C12Q 1/686* (2013.01); *C40B 30/00* (2013.01); *C40B 40/06* (2013.01); *C12Q 2535/122* (2013.01); *C12Q 2545/101* (2013.01)

(58) Field of Classification Search
None
See application file for complete search history.

(56) References Cited

U.S. PATENT DOCUMENTS 6,673,541 B1 * 1/2004 Klein .................. C12Q 1/6809
435/6.12

FOREIGN PATENT DOCUMENTS

| EP | 1109938 B1 | 2/2002 | |
| WO | WO-2009051842 A2 * | 4/2009 | ........... C12Q 1/6886 |
| WO | WO-2010/093465 A1 | 8/2010 | |

OTHER PUBLICATIONS

Beers et al., "A multiplex PCR predictor for aCGH success of FFPE samples," British Journal of Cancer, vol. 94, pp. 333-337. (Year: 2006).*
Kitayama et al., "Estimation of the detection rate in STR analysis by determining the DNA degradation ratio using quantitative PCR," Legal Medicine, published on-line Aug. 2012, vol. 15, pp. 1-6 (Year: 2012).*
International Preliminary Report on Patentability, corresponding International Application No. PCT/IB2014/066602, dated Jun. 7, 2016.
European Search Report and Opinion for European Application No. 13195770.6, dated Feb. 4, 2014.
Office Action, European Patent Application No. 13195770.6, dated Jan. 29, 2016.
Mehes, G et al., Circulating Breast Cancer Cells are Frequently Apoptotic. American Journal of Pathology, vol. 159m, No. 1, p. 17-20, Jul. 2001.
Wyllie, AH., Glucocorticoid-induced thymocyte apoptosis is associated with endogenous endonuclease activation. Nature vol. 284, p. 555-6, Apr. 10, 1980.
Lee at al., Comparison of Whole Genome Amplification Methods for Further Quantitative Analysis with Microarray-based Comparative Genomic Hybridization. Taiwan J Obstet Gynecol. vol. 47, No. 1, pp. 32-41, Mar. 2008.
Stoecklein N.H. et al: SCOMP is Superior to Degenerated Oligonucleotide Primed-PCR for Global Amplification of Minute Amounts of DNA from Microdissected Archival Tissue Samples. American Journal of Pathology, vol. 161, No. 1, Jul. 2002.

(Continued)

Primary Examiner — Young J Kim
(74) Attorney, Agent, or Firm — Marshall, Gerstein & Borun LLP

(57) ABSTRACT

A method for determining the integrity of the genome of a sample and/or the quality of a library of DNA sequences obtained by deterministic restriction site whole genome amplification can include (a) amplifying the library of DNA sequences to produce first, second, and third PCR products each of a different size from 50 bp to 1000 bp, by PCR using at least one first primer pair, one second primer pair and one third primer pair, the primer pairs each hybridizing to a DNA sequence of the library having a length from 1000 bp to 5000 bp and corresponding to a sequence of the genome located respectively on a first, second and third chromosome arm; (b) detecting the first, second and third PCR products; (c) correlating the presence of the first, second and third PCR products with the integrity of the genome of the sample and/or the quality of the library.

10 Claims, 2 Drawing Sheets

Specification includes a Sequence Listing.

(56) References Cited

OTHER PUBLICATIONS

Arneson N. et al.: Comparison of Whole Genome Amplification methods for analysis of DNA extracted from microdissected early breast lesions in formalin-fixed paraffin-embedded tissue. International Scholarly Research Network, ISRN Oncology. vol. 2012; Article ID 710692, pp. 1-10, 2012.

E H Van Beers et al., "A Multiplex PCR Predictor for aCGH Success of FFPE Samples", British Journal of Cancer, vol. 94, No. 2, Jan. 30, 2006, pp. 333-337.

Lee Y S et al., "Comparison of Whole Genome Amplification Method for Further Quantitative Analysis with Microarray-based Comparative Genomic Hybridization", Taiwanese Journal of Obstetrics and Gynecology, Elsevier (Signapore) PTE LTD, Hong Kong Branch, HK, vol. 47,m No. 1, Mar. 1, 2008, pp. 32-41.

Buffart Tineke E et al., "DNA Quality Assessment for Array CGH by Isothermal Whole Genome Amplification", Cellular Oncology, IOS Press, London, GB, vol. 29, No. 4, Jan. 1, 2007, pp. 351-359.

International Search Report and Written Opinion for Application No. PCT/IB2014/066602 dated Feb. 13, 2015.

\* cited by examiner

SEQUENCE LISTING

<160> NUMBER OF SEQ ID NOS: 18

<210> SEQ ID NO 1
<211> LENGTH: 20
<212> TYPE: DNA
<213> ORGANISM: Homo sapiens
<220> FEATURE:
<221> NAME/KEY: source
<222> LOCATION: (1)..(20)
<223> OTHER INFORMATION: /mol_type="DNA" /note="BCR-TT-3"
    /organism="Homo sapiens"

<400> SEQUENCE: 1
tcagcctcag gactcttgtg                                        20

<210> SEQ ID NO 2
<211> LENGTH: 20
<212> TYPE: DNA
<213> ORGANISM: Homo sapiens
<220> FEATURE:
<221> NAME/KEY: source
<222> LOCATION: (1)..(20)
<223> OTHER INFORMATION: /mol_type="DNA" /note="BCR-TT-5"
    /organism="Homo sapiens"

<400> SEQUENCE: 2
cgtggacaac tacggagttg                                                    20

<210> SEQ ID NO 3
<211> LENGTH: 20
<212> TYPE: DNA
<213> ORGANISM: Homo sapiens
<220> FEATURE:
<221> NAME/KEY: source
<222> LOCATION: (1)..(20)
<223> OTHER INFORMATION: /mol_type="DNA" /note="D5S2117-3"
      /organism="Homo sapiens"

<400> SEQUENCE: 3
actgagtcct ccaaccatgg                                                    20

<210> SEQ ID NO 4
<211> LENGTH: 20
<212> TYPE: DNA
<213> ORGANISM: Homo sapiens
<220> FEATURE:
<221> NAME/KEY: source
<222> LOCATION: (1)..(20)
<223> OTHER INFORMATION: /mol_type="DNA" /note="D5S2117-5"
      /organism="Homo sapiens"

<400> SEQUENCE: 4
ccaggtgaga acctagtcag                                                    20

<210> SEQ ID NO 5
<211> LENGTH: 20
<212> TYPE: DNA
<213> ORGANISM: Homo sapiens
<220> FEATURE:
<221> NAME/KEY: source
<222> LOCATION: (1)..(20)
<223> OTHER INFORMATION: /mol_type="DNA" /note="TRP53-Ex2/3-3"
      /organism="Homo sapiens"

<400> SEQUENCE: 5
cagcccaacc cttgtcctta                                                    20

<210> SEQ ID NO 6
<211> LENGTH: 20
<212> TYPE: DNA
<213> ORGANISM: Homo sapiens
<220> FEATURE:
<221> NAME/KEY: source
<222> LOCATION: (1)..(20)
<223> OTHER INFORMATION: /mol_type="DNA" /note="TRP53-Ex2/3-5"
      /organism="Homo sapiens"

<400> SEQUENCE: 6
gaagcgtctc atgctggatc                                                    20

<210> SEQ ID NO 7
<211> LENGTH: 20
<212> TYPE: DNA
<213> ORGANISM: Homo sapiens
<220> FEATURE:
<221> NAME/KEY: source
<222> LOCATION: (1)..(20)
<223> OTHER INFORMATION: /mol_type="DNA" /note="CK12-3"
      /organism="Homo sapiens"

<400> SEQUENCE: 7
ttcatgctca gctgtgactg                                                    20

```
<210> SEQ ID NO 8
<211> LENGTH: 19
<212> TYPE: DNA
<213> ORGANISM: Homo sapiens
<220> FEATURE:
<221> NAME/KEY: source
<222> LOCATION: (1)..(19)
<223> OTHER INFORMATION: /mol_type="DNA" /note="CK12-5"
      /organism="Homo sapiens"

<400> SEQUENCE: 8
gaagatccgc gactggtac                                                  19

<210> SEQ ID NO 9
<211> LENGTH: 20
<212> TYPE: DNA
<213> ORGANISM: Homo sapiens
<220> FEATURE:
<221> NAME/KEY: source
<222> LOCATION: (1)..(20)
<223> OTHER INFORMATION: /mol_type="DNA" /note="IGF2R-3"
      /organism="Homo sapiens"

<400> SEQUENCE: 9
ggatcttggt accactcatg                                                 20

<210> SEQ ID NO 10
<211> LENGTH: 19
<212> TYPE: DNA
<213> ORGANISM: Homo sapiens
<220> FEATURE:
<221> NAME/KEY: source
<222> LOCATION: (1)..(19)
<223> OTHER INFORMATION: /mol_type="DNA" /note="IGF2R-5"
      /organism="Homo sapiens"

<400> SEQUENCE: 10
gccactgtcg aagtctgca                                                  19

<210> SEQ ID NO 11
<211> LENGTH: 22
<212> TYPE: DNA
<213> ORGANISM: Homo sapiens
<220> FEATURE:
<221> NAME/KEY: source
<222> LOCATION: (1)..(22)
<223> OTHER INFORMATION: /mol_type="DNA" /note="RUFY2-3"
      /organism="Homo sapiens"

<400> SEQUENCE: 11
cagctaggaa ctccaggaat ca                                              22

<210> SEQ ID NO 12
<211> LENGTH: 23
<212> TYPE: DNA
<213> ORGANISM: Homo sapiens
<220> FEATURE:
<221> NAME/KEY: source
<222> LOCATION: (1)..(23)
<223> OTHER INFORMATION: /mol_type="DNA" /note="RUFY2-5"
      /organism="Homo sapiens"

<400> SEQUENCE: 12
gttgagggct tcatcaacac cca                                             23

<210> SEQ ID NO 13
<211> LENGTH: 20
```

```
<212> TYPE: DNA
<213> ORGANISM: Homo sapiens
<220> FEATURE:
<221> NAME/KEY: source
<222> LOCATION: (1)..(20)
<223> OTHER INFORMATION: /mol_type="DNA" /note="SMYD1-3"
      /organism="Homo sapiens"

<400> SEQUENCE: 13
cttttccctg aaggtcttag                                                    20

<210> SEQ ID NO 14
<211> LENGTH: 19
<212> TYPE: DNA
<213> ORGANISM: Homo sapiens
<220> FEATURE:
<221> NAME/KEY: source
<222> LOCATION: (1)..(19)
<223> OTHER INFORMATION: /mol_type="DNA" /note="SMYD1-5"
      /organism="Homo sapiens"

<400> SEQUENCE: 14
gggtgacctg cttgacatc                                                     19

<210> SEQ ID NO 15
<211> LENGTH: 20
<212> TYPE: DNA
<213> ORGANISM: Homo sapiens
<220> FEATURE:
<221> NAME/KEY: source
<222> LOCATION: (1)..(20)
<223> OTHER INFORMATION: /mol_type="DNA" /note="PHACTR2-3"
      /organism="Homo sapiens"

<400> SEQUENCE: 15
tgtgagaaag acttggagtt                                                    20

<210> SEQ ID NO 16
<211> LENGTH: 20
<212> TYPE: DNA
<213> ORGANISM: Homo sapiens
<220> FEATURE:
<221> NAME/KEY: source
<222> LOCATION: (1)..(20)
<223> OTHER INFORMATION: /mol_type="DNA" /note="PHACTR2-5"
      /organism="Homo sapiens"

<400> SEQUENCE: 16
actgaacaga gcaggtctac                                                    20

<210> SEQ ID NO 17
<211> LENGTH: 21
<212> TYPE: DNA
<213> ORGANISM: Homo sapiens
<220> FEATURE:
<221> NAME/KEY: source
<222> LOCATION: (1)..(21)
<223> OTHER INFORMATION: /mol_type="DNA" /note="KRAS 91bp 5 "
      /organism="Homo sapiens"

<400> SEQUENCE: 17
ataaggcctg ctgaaaatga c                                                  21

<210> SEQ ID NO 18
<211> LENGTH: 23
<212> TYPE: DNA
<213> ORGANISM: Homo sapiens
<220> FEATURE:
<221> NAME/KEY: source
```

```
<222> LOCATION: (1)..(23)
<223> OTHER INFORMATION: /mol_type="DNA" /note="KRAS 91bp 3 "
      /organism="Homo sapiens"

<400> SEQUENCE: 18
ctgaattagc tgtatcgtca agg                                              23
```

METHOD AND KIT FOR DETERMINING THE GENOME INTEGRITY AND/OR THE QUALITY OF A LIBRARY OF DNA SEQUENCES OBTAINED BY DETERMINISTIC RESTRICTION SITE WHOLE GENOME AMPLIFICATION

CROSS-REFERENCE TO RELATED APPLICATIONS

This application is the U.S. National Phase of PCT Application No. PCT/IB2014/066602 filed Dec. 4, 2014, which claims the benefit of European application No. 13195770.6 filed Dec. 4, 2013, the respective disclosures of which are each incorporated herein by reference in their entireties.

The present invention relates to a method and a kit for determining the integrity of the genome of a sample, in particular a single cell, and/or the quality of a library of DNA sequences obtained by deterministic restriction site whole genome amplification (DRS-WGA) of the genome of the sample.

STATE OF THE ART

Whole Genome Amplification (WGA) permits detection of somatic mutations and copy alterations in DNA of limited starting material, such as in the case of single circulating tumour cells (CTC) of cancer patients or in preimplantation diagnostics.

For the diagnostic use of WGA for single cell analysis, quality of genomic DNA (i.e. genome integrity) of the single cell sample of interest plays a major role for successful molecular analysis after WGA.

In particular, CTCs have been described as being frequently apoptotic (Mehes, G., et al., Circulating breast cancer cells are frequently apoptotic. Am J Pathol, 2001. 159(1): p. 17-20).

Moreover, during caspase-mediated apoptosis genomic DNA is fragmented into small pieces of 180 bp to 200 bp length (Wyllie, A H., Glucocorticoid-induced thymocyte apoptosis is associated with endogenous endonuclease activation. Nature, 1980. 284(5756): p. 555-6).

It is thus important to assess the Genome Integrity status of a single cell, as this can be linked to the biological status of the cell itself, and give clinically relevant information on the overall status of a cancer patient, which goes beyond the information provided by just counting the CTCs and complements the molecular characterization of those CTCs.

Besides, DNA crosslinking and/or fragmentation occur with chemical treatment (e.g. fixation) applied on patient-derived cells and tissues for needed sample conservation after biopsy.

To predict performance of molecular assays for single cell analysis and evaluation of resulting data derived from such samples, assessing the genomic integrity of single cells is of paramount importance.

Available single cell WGA kits assess quality of whole genome amplification by measuring the concentration of the WGA product only. As protocols for these methods include at least one random step during the procedure of single cell DNA amplification, specific assays to evaluate genome integrity of the input sample (in general a single cell) such as apoptotic or non-apoptotic status, or the quality of the output of the WGA product, such as the suitability for further genetic analysis, are difficult.

A specific kind of WGA is deterministic restriction site whole genome amplification (hereinafter referred to as DRS-WGA). DRS-WGA, which is known from EP1109938 and is commercialised as Ampli1™ by Silicon Biosystems Spa, is based on specific restriction digestion of double stranded DNA at MseI sites (TTAA) and ligation of a universal adaptor for amplification.

DRS-WGA has been shown to be better for the amplification of single cells (see for example: Lee Y S, et al: Comparison of whole genome amplification methods for further quantitative analysis with microarray-based comparative genomic hybridization. Taiwan J Obstet Gynecol. 2008, 47(1):32-41) and also more tolerant to DNA degradation due to fixative treatment (see for example: Stoecklein N. H. et al: SCOMP is Superior to Degenerated Oligonucleotide Primed-PCR for Global Amplification of Minute Amounts of DNA from Microdissected Archival Samples. American Journal of Pathology 2002, Vol. 161, No. 1; Arneson N. et al.: Comparison of Whole Genome Amplification methods for analysis of DNA extracted from microdissected early breast lesions in formalin-fixed paraffin-embedded tissue. ISRN Oncol. 2012; 2012; 710692).

To date there are no specific assays to evaluate the genome integrity of an input sample from the DRS-WGA product or the quality of the DRS-WGA product obtained.

A need is therefore felt to develop methods and kits allowing to determine the genome integrity of an input sample and/or the quality of the DRS-WGA product obtained and permitting to predict performance of molecular assays downstream of DRS-WGA for single cell analysis and evaluation of resulting data.

An object of the present invention is therefore to provide a method for determining the integrity of the genome of a sample and/or the quality of a library of DNA sequences obtained by DRS-WGA that provides robust and reliable results and allows in particular to assess the biological status of a cell/cells of the sample and/or predict the performance of molecular assays downstream of the DRS-WGA.

This object is achieved by the present invention as it relates to a method as defined in claim 1.

It is a further object of the present invention to provide a kit as defined in claim 8.

Definitions

Unless defined otherwise, all technical and scientific terms used herein have the same meaning as commonly understood by one of ordinary skill in the art to which this invention pertains.

By the term "sample", there is intended a sample comprising at least one particle of a biological entity, said particle comprising at least a DNA sequence representing the genome or a substantial subset of the genome of that biological entity. By way of non-limiting example, said entity may be a human, said at least one particle may be a set of 5 cells or less, a single cell, or a single-cell nucleus, or a haploid germ cell, or a chromosome.

By the term "genome" there is intended the entire genome or said substantial subset of the genome.

By the term "integrity" of the genome there is intended the absence of DNA damages such as double strand breaks, or nicks or similar conditions which may hamper the replication of the genome or its normal functionality.

By the term "quality" of a library of DNA sequences there is intended the suitability of the library of DNA sequences to be used for the genetic characterization of certain features such as, by way of non-limiting example, the presence of point mutations, deletions, insertions, copy number variations.

DETAILED DESCRIPTION OF THE INVENTION

Figure 1:
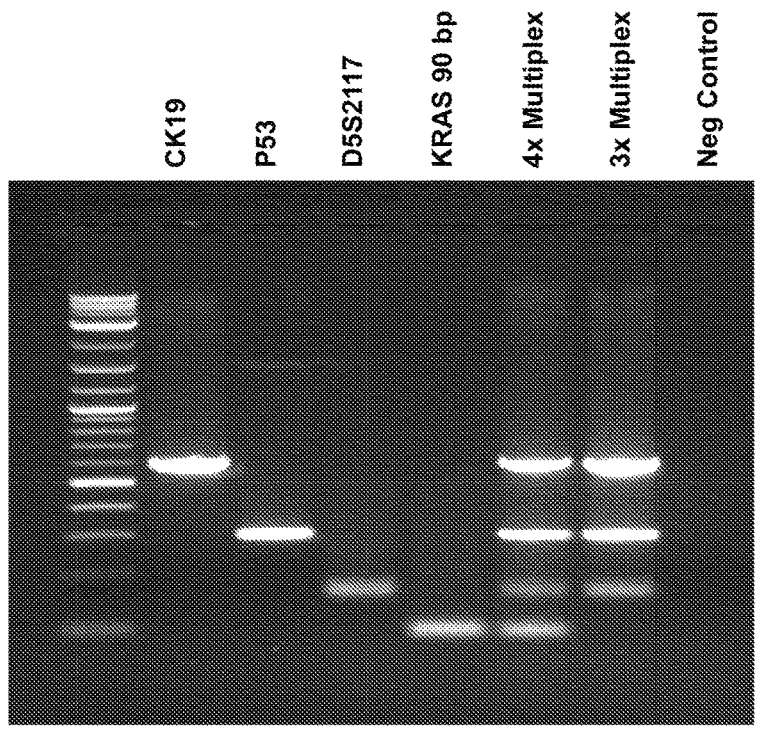
FIG. 1 shows an agarose gel picture of single marker PCRs, and of a 4-multiplex assay and a 3-multiplex assay according to preferred embodiments of the present invention.

The method according to the present invention for determining the integrity of the genome of a sample and/or the quality of a library of DNA sequences obtained by deterministic restriction site whole genome amplification (DRS-WGA) of the genome of the sample comprises steps (a) to (d).

By allowing the determination of the integrity of the genome of a sample and/or the quality of a library of sequences obtained by DRS-WGA of the genome of the sample, the method also allows to assess the biological status of of a cell/cells of the sample and/or predict the success rate of genetic analysis assays on the library of DNA sequences.

The sample preferably consists of 5 cells or less, more preferably the sample is a single cell. The single cell is preferably a circulating tumour cell (CTC), a circulating fetal cell, a circulating endothelial cell (CEC), an oocyte, a cumulus cell, a sperm, a blastomere, or a trophectoderm cell.

In step (a), the library of DNA sequences is provided.

In step (b), the library of DNA sequences is amplified by PCR using at least one first primer pair which hybridises to a DNA sequence of the library having a length from 1000 bp to 5000 bp, preferably from 1000 bp to 2000 bp, and corresponding to a sequence of the genome located on a first chromosome arm, the step of amplifying giving rise to a first PCR product from 50 bp to 1000 bp.

Preferably, the DNA sequence of the library to which the first primer pair hybridises encompasses the D5S2117 region of chromosome 5q.

More preferably, the forward primer of the first primer pair is SEQ ID NO:4 and the reverse primer of the first primer pair is SEQ ID NO:3.

In step (c) the first PCR product is detected. Agarose gel electrophoresis may be used to separate and detect the PCR product as well as other methods known in the art.

In step (d) the presence of the first PCR product is correlated with the integrity of the genome of the sample and/or the quality of the library of DNA sequences.

Advantageously, in step (b) at least one second primer pair is used which hybridises to a DNA sequence of the library having a length from 1000 bp to 5000 bp, more preferably from 1000 bp to 2000 bp, and corresponding to a sequence of the genome located on a second chromosome arm other than the first chromosome arm, the step of amplifying giving rise to a second PCR product from 50 bp to 1000 bp having a size other than the first PCR product.

The second PCR product is also detected in step (c) and the presence of the second PCR product is also correlated with the integrity of the genome of the sample and/or the quality of the library of DNA sequences in step (d).

Preferably, the DNA sequence of the library to which the second primer pair hybridises encompasses exons 2 and 3 of the TRP53 gene.

More preferably, the forward primer of the second primer pair is SEQ ID NO:6 and the reverse primer of second primer pair is SEQ ID NO:5.

Advantageously, in step (b) at least one third primer pair is used which hybridises to a DNA sequence of the library having a length from 1000 bp to 5000 bp, more preferably from 1000 bp to 2000 bp, and corresponding to a sequence of the genome located on a third chromosome arm other than the first and second chromosome arms, the step of amplifying giving rise to a third PCR product from 50 bp to 1000 bp having a size other than the first and second PCR products.

The third PCR product is also detected in step (c) and the presence of the third PCR product is also correlated with the integrity of the genome of the sample and/or the quality of the library of DNA sequences in step (d).

Preferably, the DNA sequence of the library to which the third primer pair hybridises encompasses the KRT19 pseudo-gene 1 (indicated for short as CK19).

More preferably, the forward primer of the third primer pair is SEQ ID NO:8 and the reverse primer of the third primer pair is SEQ ID NO:7.

Even more preferably, in step (b) at least one fourth primer pair is used which hybridises to a DNA sequence of the library having a length from 80 bp to 300 bp, the step of amplifying giving rise to a fourth PCR product from 50 bp to 200 bp having a size other than the first, the second and the third PCR products.

When step (b) uses at least one fourth primer pair, the fourth PCR product is also detected in step (c) and the presence of the fourth PCR product is also correlated with the integrity of the genome of the sample and/or the quality of the library of DNA sequences in step (d).

Preferably, the DNA sequence of the library to which the fourth primer pair hybridises encompasses codons 12 and 13 of the KRAS gene.

Even more preferably, the forward primer of the fourth primer pair is SEQ ID NO:17 and the reverse primer of the fourth primer pair is SEQ ID NO:18.

According to the present invention there is also provided a kit for determining the integrity of the genome of a sample and/or the quality of a library of DNA sequences obtained by deterministic restriction site whole genome amplification (DRS-WGA) of the genome of the sample comprising:

at least one first primer pair which hybridises to a DNA sequence of the library having a length from 1000 bp to 5000 bp and corresponding to a sequence of the genome located on a first chromosome arm, at least one second primer pair which hybridises to a DNA sequence of the library having a length from 1000 bp to 5000 bp and corresponding to a sequence of the genome located on a second chromosome arm other than the first chromosome arm, at least one third primer pair which hybridises to a DNA sequence of the library having a length from 1000 bp to 5000 bp and corresponding to a sequence of the genome located on a third chromosome arm other than the first and second chromosome arms, wherein the first, second and third primer pairs give rise, when amplified by PCR, to PCR products having different size from one another.

Preferably, the kit further comprises at least one fourth primer pair which hybridises to a DNA sequence of the library having a length from 80 bp to 300 bp, wherein the first, second, third and fourth primer pairs give rise, when amplified by PCR, to PCR products having different size from one another.

More preferably, the kit comprises the first, second, third and fourth primer pairs.

The kit may be used for predicting the success of a genetic analysis assay after amplification of single cell genomic DNA by DRS-WGA. Preferably the genetic analysis assay is Sanger sequencing for mutation analysis, assessment of specific copy number changes, quantitative PCR for gene amplification, metaphase Comparative Genomic Hybridisation (CGH), or array Comparative Genomic Hybridisation (CGH).

For gene specific assays, such as Sanger sequencing for mutation analysis, samples with at least 1-2 out of 4 PCR products can be used. Positivity to at least 3 out of 4 PCR products is predictive of successful genome-wide analysis with metaphase CGH. For array CGH it is advisable to use samples with 4 out of 4 positive PCR products.

The kit may also be used to determine the integrity of the genome of a sample and thus determine the biological status of the cell/cells of the sample. The sample preferably consists of 5 cells or less, more preferably the sample is a single cell.

As a matter of fact, if there is a large number of cells in the sample, there will be, overall, enough template copies for the first, second, third (and optionally fourth) primer pairs to amplify respectively the first, second, third (and optionally fourth) PCR products even if the DNA of the cells of the sample is highly fragmented. The result is the loss of the discrimination power of the method.

On the other hand, it has been experimentally determined that, even in the case of very damaged DNA cell samples, 5 cells is an amount that allows reliable results with the method, i.e allows to obtain the PCR products of step (d) without them being a results of excess template copies.

Further, for the analysis of very damaged DNA cell samples (for which single cells could result in PCR products not being amplified), the use of a number of cells greater than one, i.e. two to five, allows to quantify genome integrity thus increasing the power of resolution of the method.

EXAMPLES

In brief, several primer pairs designed on MseI fragments located on different chromosomal locations and with varying fragment lengths were tested. Three primer pairs that predict successful whole genome analysis of single cell products with high specificity and sensitivity were selected (Example 1). A fourth primer pair of a shorter MseI fragment was added to indicate successful DRS-WGA of low quality cells, e.g. apoptotic CTCs (Example 2). In the examples, PCR products are also referred to as "markers" and PCP amplification reactions including several primer pairs are also referred to as "multiplex assays". In particular, PCR amplification reactions including several primer pairs designed to determine the integrity of the genome of a sample and/or the quality of the library of DNA sequences obtained by deterministic restriction site whole genome amplification (DRS-WGA) of the genome of the sample are also referred to as "quality control assays" or "QC assays".

Example 1

Two alternative marker combinations were shown to predict the success of metaphase comparative genomic hybridization (CGH) after amplification of single cell genomic DNA with DRS-WGA (Resolution 10-20 Mb) on both cancer cell samples and samples of diploid cells with normal karyotype.

A. Characteristics of the 8 Tested PCR Markers

PCRs on 8 different MseI-fragments covering an MseI-fragment length from 239-1936 bp were tested (Table 1). Sequences located on 7 different chromosome arms were selected to minimize the chance of a negative assay result because of genomic DNA loss in a single cancer cell.

| Pipetting scheme (1x) | 1.0 µl | Buffer + dNTPs (10 mM MgCl, 100 mM Tris (pH 8.5), 500 mM KCl, 1 mM dNTPs) |
|---|---|---|
| | 0.5 µl | Primer 3' (8 µM) |
| | 0.5 µl | Primer 5' (8 µM) |
| | 0.25 µl | BSA (for molecular biology) |
| | 7.25 µl | PCR-H$_2$O |
| | 0.1 µl | Taq polymerase (5 U/µl) |
| | 0.5 µl | Ampli1 product (test sample) |

| Thermal profile | | |
|---|---|---|
| Step 1 | 94.0° C. | 2 min |
| Step 2 | Annealing Temp | 30 s |
| Step 3 | 72.0° C. | 2 min |
| Step 4 | 94.0° C. | 15 s |
| Step 5 | Annealing Temp | 30 s |
| Step 6 | 72.0° C. | 20 s |
| 14 additional cycles (steps 4-6) | | |
| Step 7 | 94.0° C. | 15 s |
| Step 8 | Annealing Temp | 30 s |
| Step 9 | 72.0° C. | 30 s |
| 24 additional cycles (steps 7-9) | | |
| Step 10 | 72.0° C. | 2 min |
| Step 11 | 4° C. | forever |

TABLE 1

Features of the 8 selected PCR primer pairs tested for the QC assay to assess DRS-WGA quality

| Primer name | SEQ ID NO | Sequence | Annealing temperature | Chromosome | Mse-fragment length | PCR-fragment length |
|---|---|---|---|---|---|---|
| BCR-TT-R | 1 | TCAGCCTCAGGACTCTTGTG | 61° C. | 22q | 1936 bp | 323 bp |
| BCR-TT-F | 2 | CGTGGACAACTACGGAGTTG | 61° C. | 22q | 1936 bp | 323 bp |

TABLE 1-continued

Features of the 8 selected PCR primer pairs tested for the QC assay to assess DRS-WGA quality

| Primer name | SEQ ID NO | Sequence | Annealing temperature | Chromosome | Mse-fragment length | PCR-fragment length |
|---|---|---|---|---|---|---|
| D5S2117-R | 3 | ACTGAGTCCTCCAACCATGG | 58° C. | 5q | 1376 bp | 140 bp* |
| D5S2117-F | 4 | CCAGGTGAGAACCTAGTCAG | 58° C. | 5q | 1376 bp | 140 bp* |
| TRP53-Ex2/3-R | 5 | CAGCCCAACCCTTGTCCTTA | 58° C. | 17p | 1374 bp | 299 bp |
| TRP53-Ex2/3-F | 6 | GAAGCGTCTCATGCTGGATC | 58° C. | 17p | 1374 bp | 299 bp |
| CK19-R | 7 | TTCATGCTCAGCTGTGACTG | 58° C. | 6q | 1146 bp | 614 bp |
| CK19-F | 8 | GAAGATCCGCGACTGGTAC | 58° C. | 6q | 1146 bp | 614 bp |
| IGF2R-R | 9 | GGATCTTGGTACCACTCATG | 58° C. | 6q | 647 bp | 217 bp |
| IGF2R-F | 10 | GCCACTGTCGAAGTCTGCA | 58° C. | 6q | 647 bp | 217 bp |
| RUFY2-R | 11 | CAGCTAGGAACTCCAGGAATCA | 64° C. | 10q | 458 bp | 104 bp |
| RUFY2-F | 12 | GTTGAGGGCTTCATCAACACCCA | 64° C. | 10q | 458 bp | 104 bp |
| SMYD1-R | 13 | CTTTTCCCTGAAGGTCTTAG | 55° C. | 2p | 287 bp | 163 bp |
| SMYD1-F | 14 | GGGTGACCTGCTTGACATC | 55° C. | 2p | 287 bp | 163 bp |
| PHACTR2-R | 15 | TGTGAGAAAGACTTGGAGTT | 58° C. | 6q | 239 bp | 205 bp |
| PHACTR2-F | 16 | ACTGAACAGAGCAGGTCTAC | 58° C. | 6q | 239 bp | 205 bp |

This primer pair amplifies a microsatellite sequence. Therefore the actual fragment length can vary slightly between alleles of one patient and between different patients.

B. Selection of PCR Markers for the QC Assay

To select the best possible combination of PCR markers, 72 single cell genomes from different types of human cancers (24 breast disseminated cancer cells (DCCs) 24 prostate DCCs, 24 melanoma DCCs) were re-amplified. For each of the three groups, 12 cells were included which resulted in successful metaphase hybridization in a previous CGH experiment and 12 cells which resulted in a failed metaphase hybridization in a previous CGH experiment. Specific PCRs for all selected markers were performed and the assay was evaluated for accuracy in predicting the outcome of metaphase CGH.

As single markers, PCRs on the long Mse-fragments D5S2117, TRP53-Ex2/3 and KRT19 pseudogene 1 (hereinafter also referred to as CK19) provided best separation between amplified genomes with successful and failed metaphase CGH. An assay of these three fragments showed high assay accuracy in predicting the success of metaphase CGH. The addition of the PCR on the shortest Mse-fragment PHACTR2 slightly increased the assay accuracy in the collective of 72 DCC genomes.

In summary, two alternative QC assays for the QC kit for Ampli1 were developed (Table 2).

Alternative 1: QC assay with 3 markers (D5S2117, TRP53-Ex2/3 and CK19).

Alternative 2: QC assay with 4 markers (D5S2117, TRP53-Ex2/3, CK19 and PHACTR2).

TABLE 2

Assay accuracy of two alternative marker combinations for the QC assay (72 DCC samples)

| Statistical measurement | Alternative 1 | | Alternative 2 | |
|---|---|---|---|---|
| | 2/3 PCRs+ | 3/3 PCRs+ | 3/4 PCRs+ | 4/4 PCRs+ |
| True+ | 35 | 29 | 35 | 29 |
| False− | 1 | 7 | 1 | 7 |
| True− | 34 | 36 | 35 | 36 |
| False+ | 2 | 0 | 1 | 0 |
| Sensitivity | 0.97 | 0.81 | 0.97 | 0.81 |
| Specificity | 0.94 | 1.0 | 0.97 | 1.0 |
| Positive predictive value | 0.95 | 1.0 | 0.97 | 1.0 |
| Negative predictive value | 0.97 | 0.84 | 0.97 | 0.84 |

If possible, only samples that are of the highest quality and that are positive for all selected markers (for both alternative assays 100% specificity) should be used. However, the trade-off for applying this high standard of quality control is a high rate of false negatives (7/36=19.4%). If the number of test samples with the highest quality standard is limited, DRS-WGA amplified genomes with ⅔ or ¾ positive PCRs still predict a high success rate for metaphase CGH (specificity 0.94 for assay with 3 markers and 0.97 for assay with 4 markers, respectively).

C. Testing of PCR Markers on a Set of 100 Diploid Cells with Normal Karyotype

To further test the set of PCR markers for the QC assay, 100 single cell genomes from diploid cells with normal karyotypes were re-amplified. All samples were tested for the 8 different PCR markers. Additionally, metaphase CGH success was checked for 22 genomes with predicted good quality and 10 genomes with predicted bad quality. The results of the statistical evaluation of assay accuracy are shown in Table 3.

TABLE 3

Assay accuracy of two alternative marker combinations for the Ampli1 QC kit (32 normal samples)

| Statistical measurement | Alternative 1 | | Alternative 2 | |
|---|---|---|---|---|
| | 2/3 PCRs+ | 3/3 PCRs+ | 3/4 PCRs+ | 4/4 PCRs+ |
| True+ | 22 | 21 | 22 | 21 |
| False− | 0 | 1 | 0 | 1 |
| True− | 10 | 10 | 10 | 10 |
| False+ | 0 | 0 | 0 | 0 |
| Sensitivity | 1.0 | 0.95 | 1.0 | 0.95 |
| Specificity | 1.0 | 1.0 | 1.0 | 1.0 |
| Positive predictive value | 1.0 | 1.0 | 1.0 | 1.0 |
| Negative predictive value | 1.0 | 0.91 | 1.0 | 0.91 |

D. Further Validation of Selected QC Markers on DRS-WGA Amplified Samples

As the tested samples in B and C were taken from an existing biobank of single cell genomes, they were amplified with DRS-WGA customized reagents of the related labs (provided by different suppliers). To validate the performance of the proposed QC assay with samples amplified by Ampli1 kit (as provided by Silicon Biosystems), single mononuclear PBLs and cell pools of a healthy donor and single cells and cell pools of the breast cancer cell line SKBR3 were isolated. The markers proposed in B and C for the QC assay were used to predict quality of the amplified genomes. Then, metaphase CGH experiments for a set of samples (5 single cells, 1 cell pool and 1 Ampli1 negative control) for diploid blood cells as well as SKBR3 cells were performed to validate the predictive accuracy of the QC assay.

SKBR: 10/11 single cells and both cell pools showed 4/4 positive bands marker PCRs
1/11 cells was negative for all tested markers negative control clean in all tested PCRs
PBL: 11/11 single cells and both cell pools showed 4/4 positive bands marker PCRs
negative control clean in all tested PCRs Example 2

As other downstream analyses, e.g. Sanger sequencing for specific fragments, are not dependent on a quantitatively and qualitatively very high amplification of the single cell DNA, a fourth fragment was included. Experiments were carried out to test whether a successful amplification of this sequence only is enough to predict success of Sanger sequencing of comparable Mse fragments (here PIK3CA hotspots 1 and 2).

A. Protocol for 4-Multiplex Assay

In order to have compatibility with the already established 3-multiplex assay, new primers were designed for the KRAS Mse-fragment encompassing the frequently mutated nucleotides encoding for codons 12 and 13. These primers amplify a PCR fragment of 91 bp length clearly distinguishable from the other three bands (D5S2117, CK19 and TP53-Exon2/3, see FIG. 1).

The following pipetting scheme and thermal profile were used adding the following KRAS primers in a concentration of 4 µM to the primer mix.

```
KRAS91bp-F       ATAAGGCCTGCTGAAAATGAC     (SEQ ID NO: 17)

KRAS91bp-R       CTGAATTAGCTGTATCGTCAAGG (SEQ ID NO: 18)

Pipetting        1.0 µl                    Ampli1 ™ PCR Reaction Buffer
scheme (1x)                                (20 mM MgCl2 included)

0.2 µl                    dNTPs (10 mM)

1.0 µl                    Primer mix (8 primers, each 4µ/M)

0.2 µl                    BSA (20 mg/ml)

6.5 µl                    PCR-H₂O 0.1 µl                    Ampli1 ™ Taq polymerase (5U/µl)

1.0 µl                    Ampli1 ™ product (test sample)

Thermal profile Step 1                     95.0° C. 4 min

Step 2                    95.0° C. 30 s

Step 3                    58.0° C. 30 s

Step 4                    72.0° C. 90 s 32 cycles (steps 2-4)

Step 5                    72.0° C. 7 min

Step 6                     4.0° C. forever
```

5 μl of each PCR product were loaded on a 1.2% agarose gel. The results were checked by comparing the obtained amplicons bp length with the expected ones, as shown in table 4.

TABLE 4

PCR product identification

| Target | Primer marker | Chromosome | Amplicon length (bp) |
|---|---|---|---|
| A | KRAS | 12p | 91 |
| B | D5S2117 | 5q | 108-166 |
| C | TRP53 | 17p | 299 |
| D | KRT19 pseudo-gene 1 (CK19) | 6q | 614 |

As already noted above, marker B maps on a polymorphic region, therefore the PCR products may be:
homozygous, and show one band of a bp comprised in the described range (108-166);
heterozygous and show two bands of different bp comprised in the described range (108-166).

Figure 3:
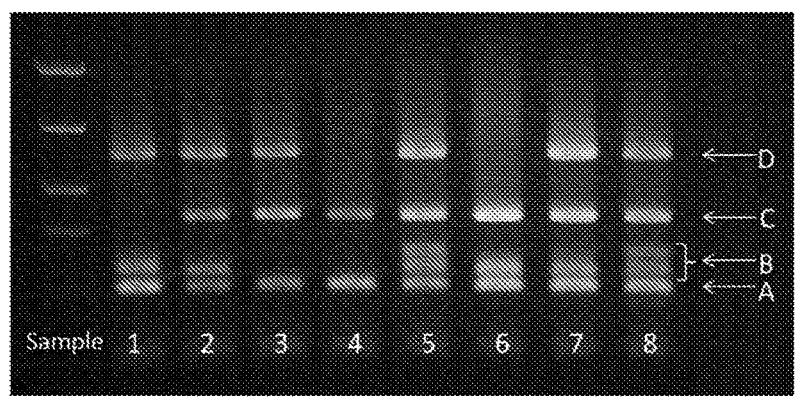
FIG. 3 shows an agarose gel picture of 8 samples tested by the preferred 4-multiplex assay of FIG. 1.

FIG. 3 shows an example of an agarose gel electrophoresis of PCR products obtained from different samples by using the above disclosed 4 multiplex assay.

Sample 1 in FIG. 3 for example displays 3/4 positive markers. Marker B heterozygosity or homozygosity (one or two bands) must be counted as one in the evaluation of the positivity for marker B. Samples 2 and 8 for example display 4/4 positive markers.

B. Comparison of 4-Multiplex Assay with Results of Single Fragment PCR Reactions and Established 3-Multiplex 72 DRS-WGA libraries of breast, prostate and melanoma DCC that had already been tested by the 3-multiplex assay of Example 1 were selected. Unfortunately the sample Breast was lost due to a fissure in the reaction tube. All other 71 DRS-WGA products were additionally tested with KRAS 91 bp single PCR and the new 4-multiplex assay. In summary, 53/71 samples showed the expected band at 91 bp in single marker PCR, and all of them but one (Breast 24) showed the same band in the 4-multiplex assay. All the other bands for D5S2117, CK19 and TP53-Exon2/3 were detected in the same samples than with 3-multiplex assay. Moreover, the KRAS 91 bp amplicon was detected in all 38 samples that showed one or more bands in the currently used 3-multiplex. Additionally, 15 samples were identified that were negative for D5S2117, CK19 and TP53-Exon2/3 but positive for KRAS91 bp, only. Finally 18 samples were negative for all four tested amplicons.

C. PIK3CA Sequencing of Ten Selected Samples

Figure 2:
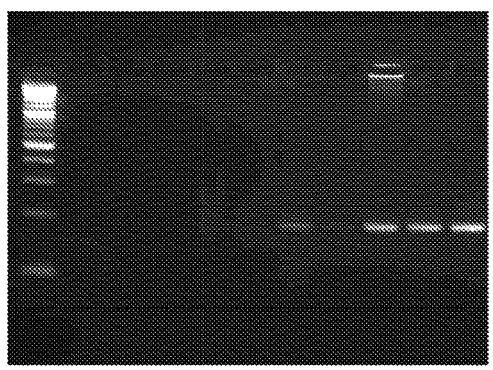
FIG. 2 shows an agarose gel picture of PCRs on PIK3CA hotspot 1 and hotspot2 (M=size marker, 01=breast13, 02=breast15, 03=breast17, 04=breast20, 05=prostate14, 06=prostate16, 07=prostate24, 08=melanoma13, 09=melanoma14, 10=melanoma16)
Figure 2:
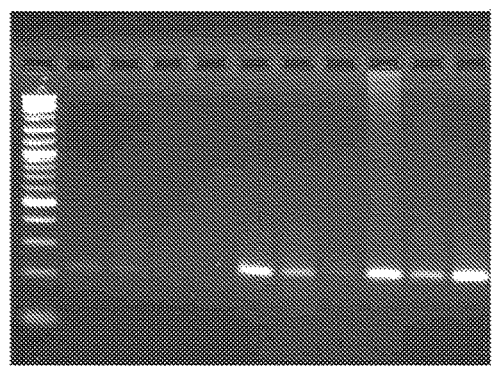

Out of the 15 samples which showed the KRAS 91 bp amplicon only, ten samples were selected for PIK3CA sequence analysis (4 breast DCC samples, 3 prostate DCC samples, and 3 melanoma. DCC samples). PIK3CA PCRs were performed for HS1 and HS2 fragments, using Ampli1™ PIK3CA Seq Kit (Silicon Biosystems SpA, Italy), according to the manufacturer instructions. After PCR all samples were loaded on a 1.5% agarose gel and amplicons visualized after electrophoresis. Strong bands were obtained only for HS1 in four DCC samples (prostate DCC 16, melanoma DCCs 13, 14, and 16) and for HS2 in five DCC samples (prostate DCCs 14, and 16, melanoma DCCs 13, 14, and 16). Additionally, weak but visible bands were detected for an additional two (breast DCC 13, prostate DCC 24) and three samples (breast DCCs 13, and 15, prostate DCC 24), respectively (FIG. 2). One sample (melanoma DCC 16) showed a strong smear for DNA fragment ≥1 kb, which was also visible in all previous gels of this sample. Nevertheless, the PCR amplicon was purified for all samples and sequenced.

Sanger sequencing for PIK3CA mutational hotspots resulted in very strong and clean sequences for the samples showing strong amplification in gel electrophoresis (see FIG. 2), including sample melanoma DCC 16. Most of the other samples with lower amplicon concentration showed high background noise, although sequences could easily be edited for two additional samples for HS1 (breast DCC 13, prostate DCC 24) and four additional samples for HS2 (breast DCCs 13, 15, and 20, prostate DCC 24). For the remaining samples background signal was too high for a secure editing of the complete sequence (breast DCCs 15, 17, and 20, prostate DCC 14 for HS1; breast DCC 15 for HS2).

Figure 4:
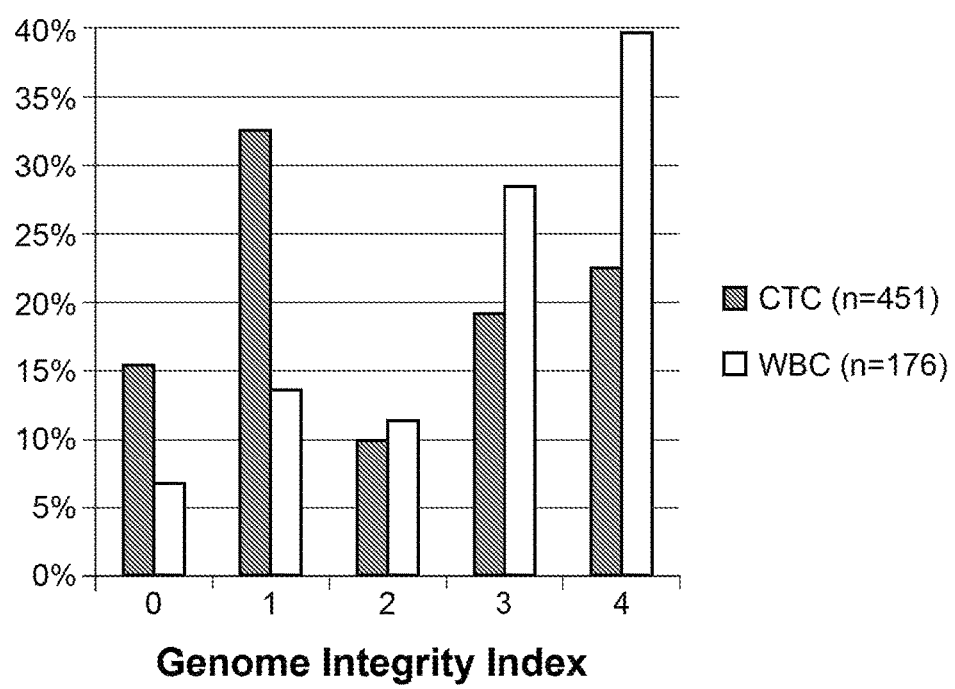
FIG. 4 shows a histogram of the distribution of the Genome Integrity Index among single Circulating Tumour Cells (CTCs) and single leukocytes (WBCs) from breast cancer patients.

On a collective of CTCs and White Blood Cells (WBCs) harvested with DEPArray™ (Silicon Biosystems SpA) from breast cancer patients peripheral blood enriched with Cell-Search® (Janssen Diagnostics LLC), the Genome Integrity was assessed by analysing the quality of Ampli1™ WGA product according to the invention. The resulting number of PCR products detected following the multiplex PCR reaction (Genome Integrity Index or GII) was found to be significantly skewed, as shown in FIG. 4, toward lower values of GII in CTCs with respect to normal WBCs collected from the same patients, undergoing the same process of enrichment sorting and Ampli1™ WGA.

By way of explanation, a GII with a value of 0 corresponds to a situation in which none of the first, second, third or fourth PCR products is amplified, a GII with a value of 1 corresponds to a situation in which only the fourth PCR product is amplified, a GII with a value of 2 corresponds to a situation in which one among the first, second and third PCR products and the fourth PCR product are amplified, a GII with a value of 3 corresponds to a situation in which two among the first, second and third PCR products and the fourth PCR product are amplified, and a GII with a value of 4 corresponds to a situation in which the first, second, third and fourth PCR products are amplified.

The GII was further used to assess the success rate of targeted Sanger sequencing for PIK3CA exon 9 and exon 20 mutation hotspots, of a custom qPCR assay to determine the amplification of ERBB2 gene, and of array CGH. Table 5

TABLE 5

| Molecular assay | Analyzed cells | Genome Integrity Index (GII) | | | | | P Value Chi-square |
|---|---|---|---|---|---|---|---|
| | | GII 0 | GII 1 | GII 2 | GII 3 | GII 4 | |
| PIK3CA HS1 | n = 383 | 7/23 (30.4%) | 14/25 (56.0%) | 48/62 (77.4%) | 102/117 (87.2%) | 146/156 (93.6%) | <0.0001 |
| PIK3CA HS2 | n = 383 | 8/23 (34.8%) | 18/25 (72.0%) | 55/62 (88.7%) | 109/117 (93.2%) | 149/156 (95.5%) | <0.0001 |
| PIK3CA complete | n = 383 | 4/23 (17.4%) | 12/25 (48.0%) | 45/62 (72.6%) | 97/117 (82.9%) | 141/156 (90.4%) | <0.0001 |

TABLE 5-continued

| Molecular assay | Analyzed cells | Genome Integrity Index (GII) | | | | | P Value Chi-square |
|---|---|---|---|---|---|---|---|
| | | GII 0 | GII 1 | GII 2 | GII 3 | GII 4 | |
| HER2 qPCR | n = 351 | 3/12 (25.0%) | 8/18 (50.0%) | 41/61 (67.2%) | 95/112 (84.8%) | 136/148 (91.9%) | <0.0001 |
| aCGH | n = 50 | Not assessed | Not assessed | 4/5 (80.0%) | 7/9 (77.8%) | 36/36 (100%) | 0.016 |

The above examples show that the method according to the present invention allows to determine the integrity of the genome of a sample and the quality of a library of DNA sequences obtained by DRS-WGA of the genome of the sample with robust and reliable results and allows in particular to predict the performance of molecular assays, such as metaphase and array comparative genomic hybridization (CGH), Sanger sequencing and qPCR, downstream of the DRS-WGA.

From an analysis of the features of the method and kit of the present invention, the resulting advantages are apparent.

In particular, in virtue of the fact that DRS-WGA is based on specific restriction digestion of double stranded DNA at MseI site (TTAA) and ligation of one universal adaptor for amplification, in principle all fragments generated during amplification that represent the WGA library are known. Thus, by the identification of specific MseI fragments having a length of >1000 bp in a single cell WGA library, the genomic integrity of the DNA of an isolated cell can be measured, and thus the quality of the sample for different kinds of successful molecular analysis determined.

Since the first, second and third primer pairs have been specifically selected in target regions of the genome corresponding to long amplicons of the DRS-WGA DNA digestion enzyme, MseI, which are more difficult to amplify in case of DNA fragmentation, their amplification is indicative of good overall success of the DRS-WGA on a given sample.

Further, in virtue of the fact that the first, second and third primer pairs are designed on different chromosome arms, the method allows to assess the integrity of the genome of a sample and/or the quality of the library of DNA sequences obtained over the broadest region of the genome.

Further, in virtue of the fact that the first, second, third and fourth PCR products have different size, it is possible to use the first, second, third and fourth primer pairs together in a multiplex reaction.

Moreover, in virtue of the fact that the fourth primer pair hybridises to a DNA sequence of the library having a length from 80 bp to 300 bp, it is possible to predict the performance of molecular assays downstream of the DRS-WGA also for low quality cells, for example apoptotic OTCs. In fact there is a significant difference in performance between the success rate in e.g. targeted sanger sequencing of the PIK3CA exon 9 (30%) and exon 20 (34%) or qPCR for Her2 CNV analysis (25%) of cells for which not even this fourth PCR product is amplified and those cells for which at least this is amplifiable, for which the success rate roughly doubles (56%, 72%, 50% respectively). The two populations would otherwise be indistinguishable when using only the 3 primer pairs hybridizing to long amplicons of the DRS-WGA.

Finally, it is clear that modifications and variants to the method and kit disclosed and shown may be made without because of this departing from the scope of protection of the appended claims.

In particular, the method may be multiplexed by using further pairs of primers which do not interfere with the PCR amplification with the first, second, third and possibly fourth primer.

The invention claimed is:

1. A method for determining the integrity of the genome of a sample to be analysed by whole genome amplification (WGA) and/or the quality of a library of DNA sequences obtained by deterministic restriction site whole genome amplification (DRS-WGA) of the genome of the sample comprising the steps of:
   (a) providing a sample having a genome
   (b) obtaining a library of DNA sequences by deterministic restriction site whole genome amplification (DRS-WGA) of the genome of the sample;
   (c) amplifying the library of DNA sequences by PCR using:
      at least one first primer pair which hybridizes to a DNA sequence of the library having a length from 1000 bp to 5000 bp and encompassing the D5S2117 region of chromosome 5q,
      at least one second primer pair which hybridizes to a DNA sequence of the library having a length from 1000 bp to 5000 bp and encompassing exons 2 and 3 of the TRP53 gene of the genome, and
      at least one third primer pair which hybridizes to a DNA sequence of the library having a length from 1000 bp to 5000 bp and encompassing the KRT19 pseudo-gene 1 of the genome,
   wherein the step of amplifying giving rise to a first PCR product from 50 bp to 1000 bp, a second PCR product from 50 bp to 1000 bp having a size other than the first PCR product, and a third PCR product from 50 bp to 1000 bp having a size other than the first and second PCR products; and
   (d) detecting the first, second and third PCR products, wherein the presence of one or more of the first, second and third PCR products corresponds to a level of the integrity of the genome of the sample and/or the quality of the library of DNA sequences.

2. The method according to claim 1, wherein a forward primer of the at least one first primer pair is SEQ ID NO:4 and a reverse primer of the at least one first primer pair is SEQ ID NO:3.

3. The method according to claim 2, wherein step (c) further uses at least one fourth primer pair which hybridizes to a DNA sequence of the library having a length from 80 bp to 300 bp, the step of amplifying giving rise to a fourth PCR product from 50 bp to 200 bp having a size other than the first, the second and the third PCR products;
   step (d) further comprises detecting the fourth PCR product;
   wherein the presence of one of more of the first, second, third, and fourth PCR product corresponds to the level of the integrity of the genome of the sample and/or the quality of the library of DNA sequences.

4. The method according to claim 3, wherein the DNA sequence of the library to which the at least one fourth primer pair hybridises encompasses Codon 12/13 of the KRAS gene.

5. The method according to claim 4, wherein a forward primer of the at least one fourth primer pair is SEQ ID NO:17 and a reverse primer of the at least one first primer pair is SEQ ID NO:18.

6. The method according to claim 1, wherein a forward primer of the at least one second primer pair is SEQ ID NO:6 and a reverse primer of the at least one second primer pair is SEQ ID NO:5.

7. The method according to claim 1, wherein a forward primer of the at least one third primer pair is SEQ ID NO:8 and a reverse primer of the at least one third primer pair is SEQ ID NO:7.

8. The method according to claim 1, wherein the sample consists of 5 cells or less.

9. The method according to claim 1, wherein the sample is a single cell.

10. The method according to claim 1, wherein determining the integrity of the genome of the sample allows to determine the biological status of the cell/cells of the sample.

* * * * *